United States Patent [19]
Noguchi et al.

[11] Patent Number: 5,330,429
[45] Date of Patent: Jul. 19, 1994

[54] CATHETER WITH A BALLOON REINFORCED WITH COMPOSITE YARN

[75] Inventors: Noriyasu Noguchi, Shiga; Yoshiharu Yamazaki, Ohtsu; Mitsuyuki Hagio, Kamakura; Yasuhiko Futami, Tokyo, all of Japan

[73] Assignee: Toray Industries, Inc., Tokyo, Japan

[21] Appl. No.: 2,422

[22] Filed: Jan. 8, 1993

Related U.S. Application Data

[63] Continuation of Ser. No. 666,987, Mar. 11, 1991, Pat. No. 5,201,706.

[30] Foreign Application Priority Data

Sep. 5, 1989 [JP] Japan .................................. 1-116607

[51] Int. Cl.$^5$ ............................................ A61M 29/02
[52] U.S. Cl. ........................................ 604/96; 606/192
[58] Field of Search ................................ 604/96–103, 604/282; 606/192–196; 600/18

[56] References Cited

U.S. PATENT DOCUMENTS

| | | | |
|---|---|---|---|
| 4,024,873 | 5/1977 | Antoshkiw et al. | 604/96 |
| 4,315,512 | 2/1982 | Fogarty | 606/194 |
| 4,327,736 | 5/1982 | Inoue | 604/101 |
| 4,608,984 | 9/1986 | Fogarty | 606/194 |
| 4,637,396 | 1/1987 | Cook | 604/99 X |
| 5,100,386 | 3/1992 | Inoue | 604/103 |

FOREIGN PATENT DOCUMENTS

| | | | |
|---|---|---|---|
| 0331040 | 9/1989 | European Pat. Off. | 604/96 |
| 0388486 | 9/1990 | European Pat. Off. | 604/96 |
| 0992072 | 1/1983 | U.S.S.R. | 604/96 |
| 1477423 | 5/1989 | U.S.S.R. | 604/96 |
| 0512456 | 9/1939 | United Kingdom | 604/96 |

*Primary Examiner*—John D. Yasko
*Assistant Examiner*—Adam J. Cermak
*Attorney, Agent, or Firm*—Armstrong, Westerman, Hattori, McLeland & Naughton

[57] ABSTRACT

A catheter with a balloon characterized by a balloon reinforced with a composite yarn consisting of an elastic yarn and a non-elastic yarn with a larger free length of the non-elastic yarn than that of said elastic yarn. When the catheter is inserted into a blood vessel or taken out on a surgical operation, the balloon is deflated to a small diameter without producing any wrinkle and is stretched by inflation to the same size and the same shape at any time. Therefore, reliability of the balloon catheter in surgical operation is improved and the cut wound in the surgical operation is smaller. Treatment and management after the surgical operation are simple and the time required for recovery is extremely short.

10 Claims, 3 Drawing Sheets

CATHETER WITH A BALLOON REINFORCED WITH COMPOSITE YARN

This is a continuation of application Ser. No. 07/666,987, filed Mar. 11, 1991, now U.S. Pat. No. 5,201,706.

BACKGROUND OF THE INVENTION

FIELD OF THE INVENTION

The present invention relates to a catheter with a balloon for expanding a constricted valve of the heart or a constricted or occluded blood vessel and thereby normalizing blood flow in a medical treatment.

BACKGROUND OF THE INVENTION

As material for the balloon for use with a catheter, thin membranes (films) of synthetic resins, such as polyethylene, polyvinyl chloride or polyester, which have no stretchability but have pressure resistance, have been used for preventing damage to blood vessels from caused by an excessive expansion. It is preferable that these balloons are not expanded, because, if they expand, the surfaces thereof become slippery and cause the balloons to slip out of, and when they are deflated, wrinkles are produced thereon which rub the inner walls of blood vessels, cause damages and accelerate formation of thrombi.

Therefore, it has been proposed, in order to improve the balloon and prevent the formation of wrinkles when deflation occurs, to use a polyurethane or a silicone as a material for the balloon (Japanese Laid-Open Patent No. 91970/1984 and No. 103,453/1986) or shrink the balloon (Japanese Laid-Open Patent No. 125,386/1978), or prevent excessive expansion or make the expansion uniform by incorporating a knitted fabric in the balloon.

In addition, it has been proposed to use rubber as a balloon material and form a guitar-shaped constricted part on the balloon by pinching the balloon with a knitted fabric having several stripes of bands for pinching a constricted valve of the heart so that the balloon does not slip out (Japanese Patent No. 23506/1982) .

However, when these balloons are used, the outer diameters become large, and exposure and incision of a blood vessel is required where the balloon is to be inserted. This results in a longer time for recovery and inconvenience after medical treatment.

On the other hand, it is proposed in Japanese Laid-Open Patent No. 103,453/1986 that a knitted fabric be put in a balloon. This requires a complicated operation consisting of knitting a parallel-twisted yarn of a polyamide yarn and a urethane yarn as a covering on the outer surface of a balloon expanded to a required expanded diameter. In addition, the diameter of the balloon cannot be made small and the balloon cannot be stretched in the longitudinal direction.

SUMMARY OF THE INVENTION

In the present invention, a balloon catheter is reinforced with a composite fiber consisting of an elastic yarn and a nonelastic yarn having a larger free length than that of the elastic yarn.

With a balloon of the present invention, larger balloon stretchability, it is possible to make the outer diameter smaller for a balloon with large expansion diameter for use in a tearing and opening technique for a heart valve. The catheter having such balloon can be inserted in a blood vessel by means of a simple Celludinga method. Therefore, the incision for a surgical insertion of the catheter can be smaller; treatment and management after the surgical operation are simple and the time required for recovery is extremely short. The burdens on the patient and the attendant are thereby reduced.

In addition, when the catheter, with a balloon of the present invention, is pushed into a blood vessel and an inner heart to a part to be treated, an inserting operation placing a guide wire and an expanded balloon in the blood flow can be easily performed because the balloon is soft, there is less possibility of damaging the inner wall of the blood vessels and workability of the catheter is good. Moreover, preparation of the cylindrical body made of a composite yarn and a cylindrical elastic film and the assembling thereof for manufacturing the balloon are easy and the yield is good and cost is lowered.

BRIEF DESCRIPTION OF THE DRAWINGS

An example of a structure of a catheter with a balloon of the present invention is described in conjunction with the appended drawings, as describer below

DESCRIPTION OF THE PREFERRED EMBODIMENT

Figure 1:
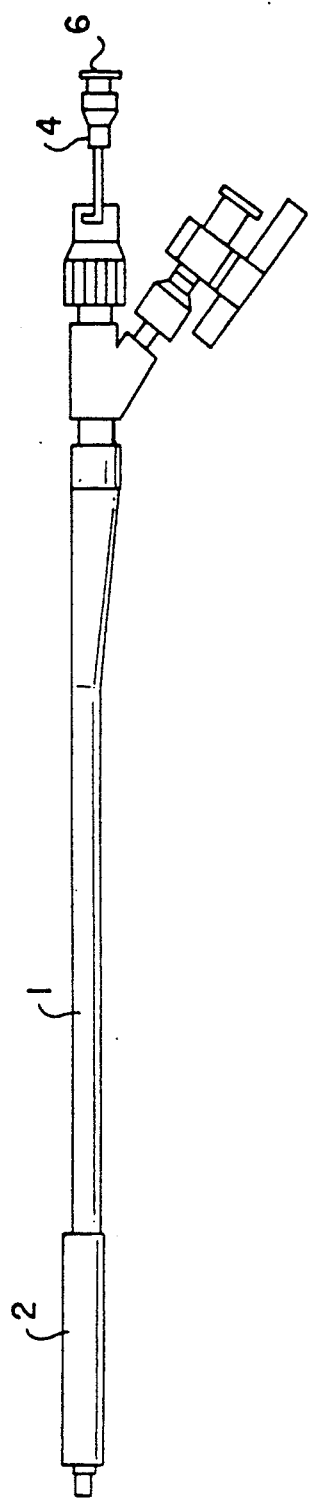
FIG. 1 is a side elevation view of a catheter with the balloon of the present invention.
Figure 2:
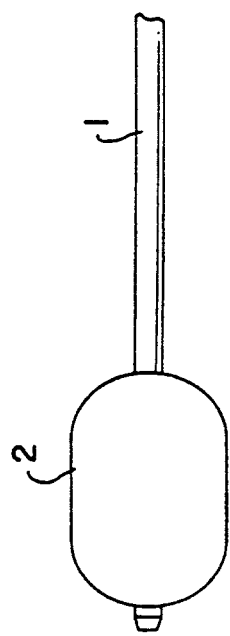
FIG. 2 is an enlarged view of the end of the catheter of FIG. 1 with the balloon part of the catheter of FIG. 1 expanded.
Figure 3:
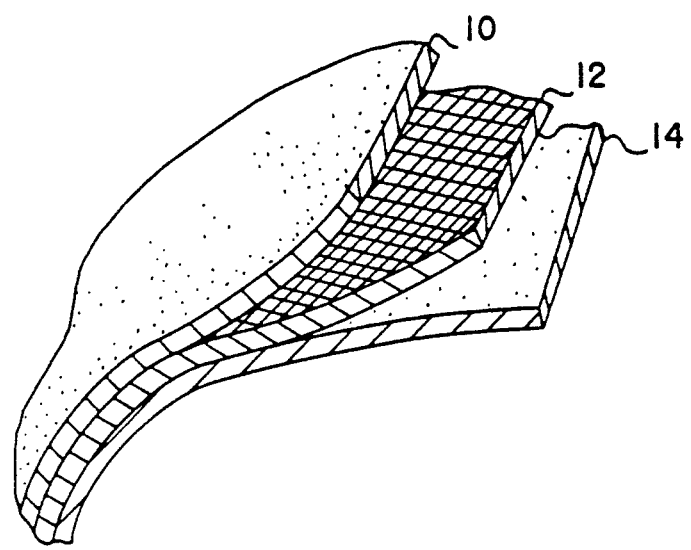
FIG. 3 is an enlarged sectional view, in perspective, of the balloon material.

As illustrated in FIG. 1, the catheter of the instant invention, includes a tube 1, with a balloon 2 constituting a three-layered structure, with a cylindrical body consisting of a cylindrical elastic film and a composite yarn and is attached on the apex of tube 1 with a smooth surface and a round cross-section. On the rear end of the tube 1, if necessary, a fluid inlet 4 and a take-up opening 6 for an air removal tube placed in a fluid transferring path are provided. In the catheter with a balloon of the present invention, the ratio of the free length of an elastic yarn to a non-elastic yarn is preferably 0.15–0.5 and more preferably 0.2–0.35. If this ratio is larger, the balloon is not sufficiently expandable, and if too small, the reinforcing effect of the non-elastic yarn is reduced and breakage of the balloon, when expanded, easily occurs. The ratio of the free length is determined by measuring a kink of the S—S curve of the composite yarn to the higher tension side. When the free length of the nonelastic yarn fluctuates and the kink is unclear, the straight lines before and behind the full length is extrapolated.

As the preferred structure of the composite yarn, a core of an elastic yarn with a sheath of a non-elastic yarn is preferable because the core and sheath yarns are hardly separated. Namely, to make the composite yarn easily stretchable by an inner pressure or to preset the stretching and the final stretched state, the yarn is performed by stretching and shrinking the yarns in advance. The possibility that constituting yarns may separate badly influences the effect of the present invention.

As the method of manufacturing the core-sheath yarn, twisting or entangling of the elastic yarn by means of a fluid, performed while a non-elastic yarn is overfed, is preferable. A core-sheath yarn made by spirally winding a twisted yarn of a synthetic fiber on an urethane yarn as it is compact and is especially preferred. As the non-elastic yarn, a textured yarn is preferable, because its stretchability, adhesiveness with an elastic film etc., are excellent. Among textured yarns, false-twisted textured yarns, with excellent stretchability, are preferable. When a non-textured yarn is used, separation thereof from an elastic yarn easily occurs, but can be avoided by increasing the number of twists.

Figure 4:
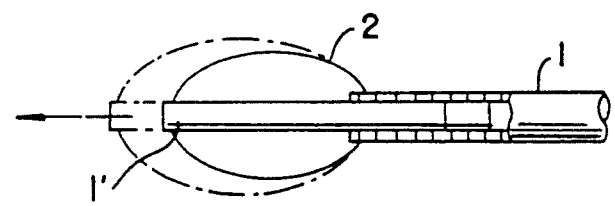
FIG. 4 is a side view, partly in section of a second embodiment of the invention.
Figure 5:
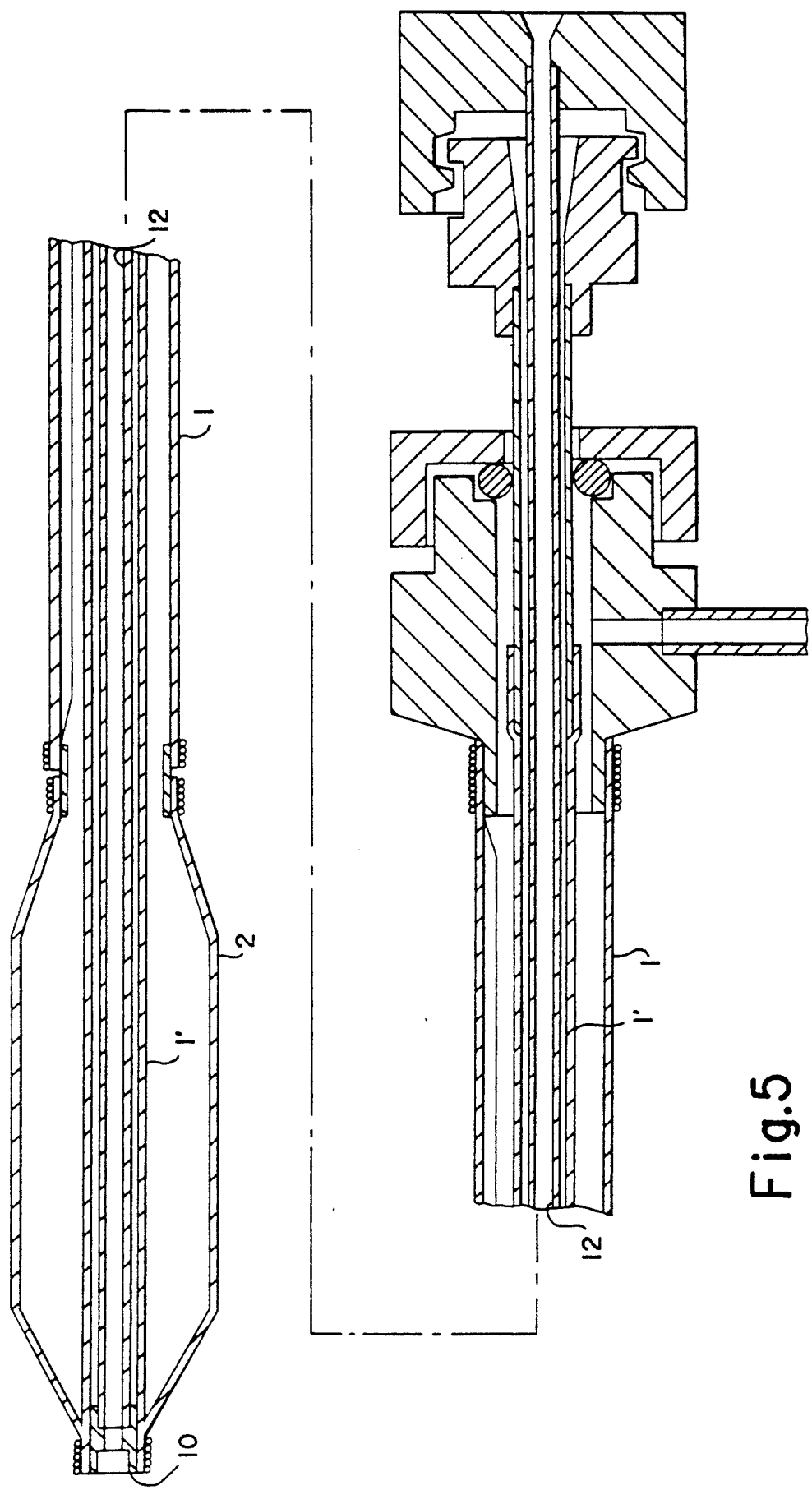
FIG. 5 is a two part side sectional view of a modification of a second embodiment of the invention.

It is preferable that the balloon consists of a three-layered structure of an outer elastic film 10, a cylindrical body 12 of a composite yarn and an inner elastic film 14. The inner elastic film 14 provides a reinforcing effect caused by the composite yarn 12. The outer elastic film 10 enables better passage through the blood vessel better. The balloon, based on the present invention, can be applied to most catheters that employ a balloon. Furthermore, excellent results can be expected when the balloon of the present invention is applied to a catheter with a balloon, as shown in FIG. 4, wherein one end of the balloon 2 is fixed on the inner tube 1' (the inner tube may be an inner-filled rod) and another end thereof is fixed on the outer tube 1 of a double tube. The inner 1' and outer 1 tubes can be concentrically slidable. Namely, in such a catheter with a balloon, the outer diameter of the balloon 2 can be decreased by sliding such tubes, thereby stretching the balloon in the axial direction when it is inserted in a blood vessel, is inside of the heart or as such catheter is removed. If the rigidity of the inner tube 1' is too small and will not stretch the balloon, the balloon can be effectively stretched in the axial direction by providing a stopper 10 on the apex of the inner tube 1' and the stopper can be pushed with a rod 12 insertable in the inner tube, as shown in FIG. 5. If the rigidity of the outer tube is insufficient, it is preferable that a high-modules fiber be fixed on the apex of the outer tube and be guided to the opposite end.

The elastic film may be made of a thin membrane with large stretchability and smooth surface in such a way that the thickness of the front end side of the film is thinner than that of the rear end. As the raw material, polyurethanes and rubbers are used. Rubbers having small initial moduli are excellent materials as raw materials for the elastic film.

The thickness of the elastic film is preferably in the range of 0.1-0.4 mm, and it is not necessarily the same thickness between the inner and the outer layers.

A difference in thickness between the front end side and the rear end side is preferably about 5-20%. Such a difference can be obtained by making the film thinner, for example, when a cylindrical elastic film is prepared, or by expanding a corresponding part of the prepared cylindrical elastic film and fixing the residual elongation thereof.

As the cylindrical body 12 made of the composite yarn, a knitted fabric, a woven fabric, a braid or a wound body in a cylindrical shape with a large twill angle can be used. A cylindrical-knitted structure, with stretchability, is preferable.

When a guitar-shaped balloon is prepared, for example, an elastic band is adhered on the middle part of an elastic body with an adhesive such as a rubber paste.

As the elastic yarn has a core yarn for a textured yarn, any fiber with stretchability can be used without specific limitation. For example, a single yarn or a twisted yarn made of a rubber, such as natural rubbers and synthetic rubbers or a polyurethane is suitable. As the yarn to be wound and made of a synthetic fiber, not only high-tenacity nylon, polyester and "Teflon" yarns but high-tenacity polyamide and polyethylene yarns can be used as a single yarn. A twisted yarn being flexible is preferable. The thicknesses of such yarns are not specifically limited, as the required pressure-resistant characteristics are different, depending upon the position to be worked and the purpose. In many cases, the thickness of the elastic yarn, as the core yarn, is selected in the range of 10-50D and that of the tenacity or high tenacity yarn to be wound is selected in the range of 30-150D.

If the outer elastic film 10 is adhered on a cylindrical body of a composite yarn and the inside of the cylindrical body of the composite yarn, between an elastic film, is coated with a silicone oil etc., a gap caused by expansion or shrinkage is not produced and a uniform expansion can be obtained. The length of the balloon 2 can be freely set and, in many cases, it is preferably in the range of 15'70 mm.

It is preferable that both ends and the apexes of balloon 2, and the connected parts with tubes 1, can be finished with an adhesive to make their surfaces smooth.

As the raw material used for a soft inner tube in coaxially (concentrically)-assembled tubes, for example, polyvinyl chloride and polyurethane are preferably used. The length of such tube is preferably 5-25 cm. It is preferable that the diameter be 14 Fr, or smaller, as it is inserted by means of the Celludinga method.

In addition, as the relatively hard outer tube with torque characteristics, for example, a tube made of a synthetic resin such as polyethylene, "Teflon" polypropylene and nylon is used. Besides these tubes can be used, for example, hard tubes, such as a tube made by extracting a plasticizer for polyvinyl chloride with a solvent or a tube cured by crosslinking by means of irradiation. It is preferable that the diameter of this outer tube is 14 Fr or smaller because of the above described reason. In addition, the length is not specifically defined, as it is different depending on age and size of the patient and the distance from the inserted part to the position to be treated, but a product with a total length in the range of 50-200 cm is preferably used.

In addition, depending on the position to be treated, a relatively hard tube similar to the outer tube 1 can be sometimes preferably substituted for the soft inner tube as the relatively hard tube provides an action making insertion of a rigid body easy.

Furthermore, if a contrast-medium, such as, barium sulfate, bismuth compound or a metal powder, such as tungsten is mixed in these tubes, it is preferable that the position in the blood vessel can be thereby detected by X-ray irradiation.

In addition, as the raw material of the yarn or the knitted fabric buried in or set along with the soft inner tube, a thin and strong yarn are preferable. For example, such yarns can be all used, but polyamide yarns are the best among them.

In addition, it is necessary that an air removal tube, set between an inner tube and an outer tube, does not interfere with the flexibility of the soft tube. A tube with a thin thickness and a small diameter, for example, a tube made of polyamide or "Teflon" or a polyethylene tube, is used.

As a rigid body inserted in an inner tube and stretching a balloon, for example, a stainless pipe or thin rod can be used.

In addition, as a fluid expanding a balloon, for example, physiological saline, carbon dioxide or a contrast-medium is used. These fluids are used by a method wherein a specified amount of fluid is injected thereinto by means of an injection cylinder, etc.

The catheter, with a balloon of the present invention, has such features that the stretchability is large and it exhibits pressure resistance and a uniform expanding property by using a cylindrical body made of a composite yarn with enlarged stretchability.

By the present invention, even a balloon with a large diameter can be inserted in a blood vessel in such a way that it is made long and slender and small and in addition, there is no possibility of damaging the inner wall of the blood vessel when the apex part of a tube rubs such wall. The balloon can be transferred to the position to be treated through the blood vessel and the heart by utilizing a guide wire and the floating property of the balloon.

The time required for treatment is short and management after surgical operation is simple and recovery can be rapidly performed. Furthermore, this method can be provided as a method wherein expansion of the occluded part of a blood vessel or an opening technique for a valve of the heart by means of a balloon can be non-operationally, simply and easily performed. In addition, the balloons of the present invention can be simply manufactured in such a way that products with various sizes are separately manufactured to provide catheter with balloons with good yield and with low cost.

EXAMPLES

The present invention will be explained in more detail by using examples as follows.

EXAMPLE 1

A false-twisted textured yarn consisting of a polyester yarn (a non-elastic yarn) of 70D-24f was intertwisted to a polyurethane yarn (an elastic yarn: "Opelon") of 20D at a speed of 400 T/m while the former was overfed 300% to said urethane yarn to manufacture a composite yarn.

The ratio of free length of said yarn was 0.26 read from the S—S curve.

A balloon was prepared by using this composite yarn.

Namely, as an outer tube, a polyethylene tube containing a contrast-medium with 13.5 Fr and a length of 560 mm and a polyvinyl chloride tube containing 45 parts of DOP dioctylphthalate with 13.5 Fr and a length of 130 mm were connected through a stainless pipe with a diameter of 3.5 mm and a stainless pipe with a diameter of 3 mm and a length of 6 mm was attached on the apex of the polyvinyl chloride tube. In this time, a polyamide twisted yarn of 400D was placed on the hollow side of the polyvinyl chloride and fixed on stainless pipes on both sides. As an inner tube, on the apex of a polyvinyl chloride tube containing 45 parts of DOP with 6.6 Fr, a stainless pipe, with a diameter of 1.6 mm and a length of 7 mm and having a projected part inside made by means of a corset, was attached and a stainless pipe with 14G and a length of 70 mm and a needle base was inserted in the rear end. Connection of the inner and outer pipes and the inserted stainless pipe were bound and fixed with a nylon yarn with a thickness of 70 μm. This inner tube was passed through a W-connector and inserted into the outer tube. The outer tube was then fixed on the W-connector to prepare a tube part.

As an inner elastic film of the balloon, rubber with a thickness of 0.25 mm and a length of 25 mm was bound and fixed on each apex of the inner tube and the outer tube with a nylon yarn with a thickness of 70 μm and the surface thereof was coated with a small amount of a silicone oil. A cylindrically-knitted fabric was separately prepared by knitting the composite yarn by means of a knitting machine wherein 50 knitting needles were arranged on a circumference with a diameter of 20 mm. On the middle part of the knitted fabric, with a length of 30 mm, rubber with a thickness of 0.25 mm and a length of 7 mm was adhered with a rubber paste to prepare a band.

On the outside thereof, a part prepared by adhering a rubber tube with a thickness on the front side of 0.25 mm and a thickness on the rear side of 0.3 mm was covered. The parts were all fitted together in such a way that the total length was 25 mm and both ends thereof were bound and fixed with a nylon yarn with a thickness of 70 μm. The excess knitted fabric and rubbers were cut off to complete a balloon part.

After a polyamide tube with a diameter of 0.9 mm was inserted into a fluid transferring path between the inner and outer tubes from one of remaining openings of the W-connector up to 10 mm to the balloon, the rear part up to the inside of the W-connector was covered with a reinforcing polyethylene tube. After a two directional stopcock was fixed on the rear end thereof and the gaps of the openings were filled with an adhesive material, the surfaces of the both ends of the balloon, the apex and the connected parts of tubes were finished smoothly with an epoxy resin to complete a catheter with a balloon of the present invention.

The catheter, with the balloon, was attached on an injection cylinder and, after water was substituted for air and, while air was evacuated from an air vent, about 7 ml of water was injected therein. Only the apex part of this balloon was expanded to about 23 mm. Then, when the injected amount was made to 23 ml, the balloon turned into a cylindrical shape with a diameter of about 28 mm.

The water was removed and the surface was smoothly shrunk without producing wrinkles. Then, a stainless steel tube with a diameter of 1.19 mm was inserted into the inner tube to push the apex part of the inner tube and to stretch the balloon from 25 mm to 55 mm. The diameter of the balloon was changed thereby from about 7 mm to 4.5 mm. When the stainless tube was pulled backward, the balloon was returned to its original diameter and length.

EXAMPLE 2

A catheter, with a balloon similar to the one of Example 1, was used for a clinical treatment for an interrelated tearing and opening technique for a mitral valve. Using a method perforating the atrium partition, a specially-made guide wire was inserted into the left atrium of a patient through the skin, the crotch vein, the right atrium and the atrium partition. Then, a dilator of 14 Fr was forwarded along with this guide and the perforated parts on the crotch vein and the atrium partition were expanded. A catheter, with a balloon of the present invention, was successively inserted into the left atrium from the right atrium through the atrium partition and only the apex of the balloon was expanded to a diameter of 10 mm by using carbon dioxide run into a valve opening with the blood flow as a Swanganz catheter. The catheter was inserted into the left ventricle. The apex side of the balloon was expanded by using a contrast-medium and was lightly drawn nearby and brought into contact with the valve opening to be torn and opened. At this position, the balloon was expanded and the valve opening was pinched with the constricted balloon. The balloon was expanded under this condition and the valve opening was enlarged without slippage out of the balloon.

The tearing and opening technique needed 1 hour containing 5 sec for expansion and shrinkage of the balloon without any side effect. Three days were needed from entering a hospital to leaving the hospital for the treatment. The time needed was less than half as compared with a tearing and opening technique accompanied with exposure and cutting-out of the blood vessel.

EXAMPLE 3

A catheter, with a balloon, was prepared in the same way as in Example 1, but the denier of "Opelon" yarn as the elastic yarn was 30D and the ratio of overfeeding a polyester yarn and the number of twist thereof were changed to 270% and 400 T/m, respectively.

In this catheter with a balloon, the ratio of free length of the constituting yarns of the composite yarn was apparently 0.28 and the balloon exhibited the maximum expanded diameter of 30 mm, the minimum shrunk diameter of 4-5 mm and excellent stretching characteristics without generation of wrinkles.

The catheter with a balloon of the present invention can be widely used in a method for medical treatment wherein a shrunk balloon is inserted into a constricted or occluded blood vessel and a fluid is pressed into the balloon to expand the balloon. The expanded balloon enlarges the constricted or the occluded blood vessel to make the constricted or occluded part normal. It can especially be widely used for a non-surgical and through-skin type valve tearing and opening operation substituting for a valve incisive operation for the valve of the heart which is constricted by aging, calcination or a sequela of rheumatic heat and a valve substitutive operation for an artificial valve.

What is claimed:

1. A balloon for use in a balloon catheter, comprising:
    an outer elastic film;
    a reinforcing fabric, comprising a composite yarn consisting of an elastic yarn and a non-elastic yarn having a larger free length than that of said elastic yarn; and
    an inner elastic film,
    wherein the reinforcing fabric and the inner elastic film are not adhered with each other, and
    wherein the reinforcing fabric is adhered with the outer elastic film.
2. A balloon as recited in claim 1, wherein the reinforcing fabric consists of a knitted fabric.
3. A balloon as recited in claim 1, wherein the reinforcing fabric consists of a woven fabric.
4. A balloon as recited in claim 1, the catheter further comprising a double tube having an inner and an outer tube concentrically slidable with each other, wherein one end of the balloon is fixed on the inner tube of said double tube and another and thereof is fixed on the outer tube.
5. A balloon as recited in claim 4, the catheter further comprising a shaft insertable in said inner tube and a stopper for said shaft on the apex of said inner tube.
6. A balloon for use in a balloon catheter, comprising:
    an outer elastic film;
    a reinforcing fabric; and
    an inner elastic film,
    wherein the reinforcing fabric and the inner elastic film are not adhered with each other,
    wherein said reinforcing fabric comprises a composite yarn consisting of an elastic yarn and a non-elastic yarn having a larger free length than that of said elastic yarn, and
    wherein the ratio of free length of said elastic yarn to said non-elastic yarn is 0.15; to 0.5
7. A balloon for use in a balloon catheter, comprising:
    an outer elastic film;
    a reinforcing fabric; and
    an inner elastic film,
    wherein the reinforcing fabric and the inner elastic film are not adhered with each other, and
    wherein said composite yarn consists of a core-sheath yarn in which the core comprises an elastic yarn and the sheath comprises a non-elastic yarn.
8. A balloon as recited in claim 7, wherein the non-elastic yarn is spirally wound on the elastic yarn.
9. A balloon as recited in claim 7, wherein the non-elastic yarn consists of a false-twisted textured yarn.
10. A balloon for use in a balloon catheter, comprising:
    an outer elastic film;
    a reinforcing fabric; and
    an inner elastic film,
    wherein the reinforcing fabric and the inner elastic film are not adhered with each other, and
    wherein the inner elastic film and the reinforcing fabric are separated by a coating of lubricant.

* * * * *